(12) United States Patent
Xu

(10) Patent No.: US 9,481,665 B2
(45) Date of Patent: Nov. 1, 2016

(54) PROCESS FOR PREPARING PI3K INHIBITOR BUPARSILIB

(71) Applicant: Yong Xu, San Diego, CA (US)

(72) Inventor: Yong Xu, San Diego, CA (US)

(*) Notice: Subject to any disclaimer, the term of this patent is extended or adjusted under 35 U.S.C. 154(b) by 0 days.

(21) Appl. No.: 14/656,774

(22) Filed: Mar. 13, 2015

(65) Prior Publication Data

US 2016/0264546 A1    Sep. 15, 2016

(51) Int. Cl.
*C07D 401/04* (2006.01)
*C07D 239/48* (2006.01)

(52) U.S. Cl.
CPC ........... *C07D 401/04* (2013.01); *C07D 239/48* (2013.01)

(58) Field of Classification Search
CPC .................................................. C07D 401/04
See application file for complete search history.

(56) References Cited

FOREIGN PATENT DOCUMENTS

WO   WO-2007/084786 A1 *  7/2007
WO   WO-2012/044727 A2 *  4/2012

OTHER PUBLICATIONS

Burger et al., ACS Medicinal Chemistry Letters, 2011, 2(10), pp. 774-779.*

* cited by examiner

*Primary Examiner* — Laura L. Stockton
(74) *Attorney, Agent, or Firm* — Kile Park Reed & Houtteman LLC

(57) ABSTRACT

The present disclosure provides a new process for preparing PI3K inhibitor buparsilib. The whole reaction route of the present invention is simple and easy to control for the industrial production.

16 Claims, No Drawings

PROCESS FOR PREPARING PI3K INHIBITOR BUPARSILIB

FIELD

The present invention refers to a chemical medicine field, it relates generally to the synthesis of PI3K inhibitor, specifically, the invention relates to new process for preparing PI3K inhibitor buparsilib.

BACKGROUND

Novartis is developing buparlisib (BKM-120; NVP-BKM-120), an oral phosphoinositide 3-kinase (PI3K) inhibitor which shows pro-apoptotic and antiangiogenic activity, for the potential treatment of solid tumors, primarily advanced breast cancer.

In August 2012, a phase III combination trial was initiated for ER+/HER-advanced breast cancer in postmenopausal women refractory to aromatase inhibitor therapy. In October 2012, a phase III combination study began in ER+/HER-advanced breast cancer in postmenopausal women after progression on an mTOR inhibitor. In July 2014, phase III development was ongoing and Novartis expected to file for approval in breast cancer patients naive to mTOR inhibitors in 2015 and those previously treated with mTOR inhibitors in 2016. A phase II trial began in triple negative breast cancer in June 2012. A phase II trial in HER2-positive breast cancer in the neoadjuvant setting began in September 2013.

Buparlisib is described chemically as 5-(2,6-dimorpholinopyrimidin-4-yl)-4-(trifluoromethyl)pyridin-2-amine, and has the structural formula shown as Formula 1:

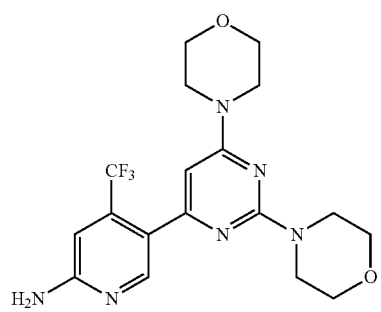

1

Buparlisib can be prepared by several methods described in prior arts, such as patents WO2007084786, WO2012044727, and so on. But the process for preparing buparlisib in the present invention disclosed herein has not yet been published.

DESCRIPTION OF THE DISCLOSURE

It is an object of the present disclosure to devise a method for preparing PI3K inhibitor to improve the process for the synthesis of PI3K inhibitor buparlisib, thereby avoiding at least one of the disadvantages described above.

According to the present disclosure, it is devised a new process of preparing buparlisib (compound 1).

The technical solutions of the present disclosure include: a compound 4 is prepared by a process comprising reacting a compound 2 with a compound 3, and buparlisib (compound 1) is prepared by a process comprising reacting a compound 6 mixed with a compound 5, then further mixed with the compound 4.

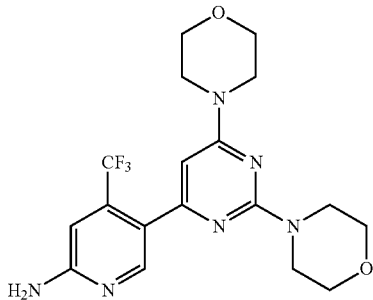

1

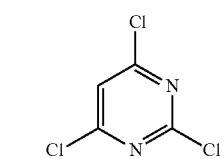

2

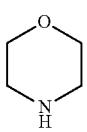

3

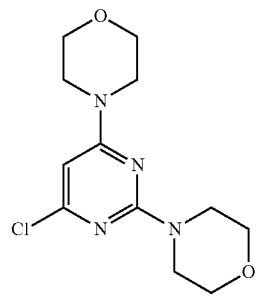

4

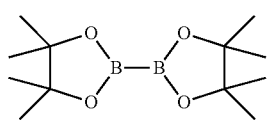

5

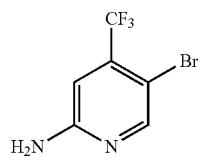

6

According to some embodiments in the method disclosed herein, the preparation method of buparlisib includes the following steps:

Step (1): contacting a compound of formula 2 with a compound of formula 3 to obtain a compound of formula 4.

Step (2): contacting a compound of formula 6 with a compound of formula 5 and the compound of formula 4 to obtain the buparlisib of formula 1.

According to some embodiments of the present disclosure, the compound of formula 2 is contacted with the compound of formula 3 in a first organic solvent and in presence of a base. According to some embodiments of the present disclosure, the first organic solvent is dichloromethane, and the base is triethanolamine.

According to some embodiments of the present disclosure, the step (1) comprising: (1-1) dissolving the compound of formula 2 and the base in the first organic solvent; (1-2)

adding a first dichloromethane solution of the compound of formula 3 into a resulting mixture of step (1-1) under a temperature ranging about −5° C. to about 0° C.; (1-3) keeping a resulting mixture of step (1-2) at room temperature for about 0.5 hour to about 2 hours; (1-4) adding a second dichloromethane solution of the compound of formula 3 into a resulting mixture of step (1-3) under a temperature ranging about −5° C. to about 0° C.; and (1-5) keeping a resulting mixture of step (1-4) at room temperature for about 1 hour to about 3 hours.

According to some embodiments of the present disclosure, the step (1) comprises, adding the compound 2, a base and $CH_2Cl_2$ into a first reactor, and lowering the temperature to −5° C.~0° C. Then, dripping a first $CH_2Cl_2$ solution of morpholine (compound 3) slowly to the first reactor, keeping the resulting mixture at room temperature for 0.5~2 hours. Then lowering the temperature to −5° C.~0° C., dripping a second $CH_2Cl_2$ solution of morpholine (compound 3) slowly to the first reactor, and keeping the mixture at room temperature for 1 hour to 3 hours. Then the resulting reaction solution is washed by saturated salt water for 2 to 3 times, dried over $Na_2SO_4$, and concentrated to obtain the compound 4. The identity and purity of the compound 2 may be confirmed by $^1H$ and $^{13}C$ NMR spectroscopic, and HPLC analysis.

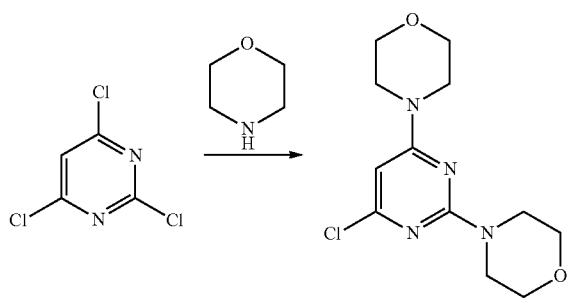 [SMILES: Clc1cc(Cl)nc(Cl)n1 ; C1COCCN1 ; Clc1cc(N2CCOCC2)nc(N2CCOCC2)n1]

According to some embodiments of the present disclosure, the step (1) comprising: (a) dissolving the compound of formula 2, 18.3 g, 0.10 mol and triethanolamine 200 ml in dichloromethane 200 ml; (b) adding a first dichloromethane solution of the compound of formula 3, 9.57 g, 0.11 mol into a resulting mixture of step (a) under a temperature of −5° C.; (c) keeping a resulting mixture of step (b) at room temperature for about 2 hours; (d) adding a second dichloromethane solution of the compound of formula 3, 8.7 g, 0.10 mol into a resulting mixture of step (c) under a temperature of −5° C.; and (e) keeping a resulting mixture of step (d) at room temperature for about 3 hours.

According to some embodiments of the present disclosure, in the method disclosed herein, in the first $CH_2Cl_2$ solution of morpholine (compound 3) in step (1-2), morpholine (compound 3) may be used at an amount of 1.0 equivalent to 1.1 equivalents per 1 equivalent by mole of the compound 2. In other embodiments, the amount is 1.05 equivalents per 1 equivalent by mole of the compound 2.

According to some embodiments of the present disclosure, in the method disclosed herein, in the second $CH_2Cl_2$ solution of morpholine (compound 3) in step (1-4), morpholine (compound 3) may be used at an amount of 1.0 equivalent to 1.1 equivalents per 1 equivalent by mole of the compound 2. In other embodiments, the amount is 1.05 equivalents per 1 equivalent by mole of the compound 2.

According to some embodiments of the present disclosure, in the method disclosed herein, the base may be triethanolamine (TEA).

According to some embodiments of the present disclosure, the compound of formula 6 is contacted with the compound of formula 5 and the compound of formula 4 in a second organic solvent, and in presence of a salt and $PdCl_2(PPh_3)_2$. According to some embodiments of the present disclosure, the second organic solvent is DMSO, and the salt is KOAc.

According to some embodiments of the present disclosure, the step (2) comprising: (2-1) dissolving the compound of formula 6, the compound of formula 5, KOAc and $PdCl_2(PPh_3)_2$ in DMSO; (2-2) keeping a resulting mixture of step (2-1) under a temperature ranging about 5° C. to about 15° C. for about 3 hours to about 7 hours; and (2-3) adding the compound of formula 4 into a mixture of step (2-2), and keeping the resulting mixture under a temperature ranging about 5° C. to about 15° C. for about 12 hours to about 18 hours.

According to some embodiments of the present disclosure, the step (2) comprises, adding the compound 6, bis(pinacolato)diboron (compound 5), DMSO, KOAc and $PdCl_2(PPh_3)_2$ into a second reactor, then heating the resulting mixture to 5° C.~15° C. and keeping the reaction for 3~7 hours, and then adding the compound 4 into the second reactor, keeping the reaction for 12~18 hours. Put the reaction solution into water after the reaction is finished, and large amount of solid are separated. The resulting mixture is filtered, stirred with methanol/acetone (V:V=1:1) and crystallized for 3 hours. The filter cake is dried in vacuo at 60° C. for 8 hours to obtain the buparlisib product (compound 1) as a white solid. The identity and purity of buparlisib (compound 1) may be confirmed by $^1H$ and $^{13}C$ NMR spectroscopic, and HPLC analysis.

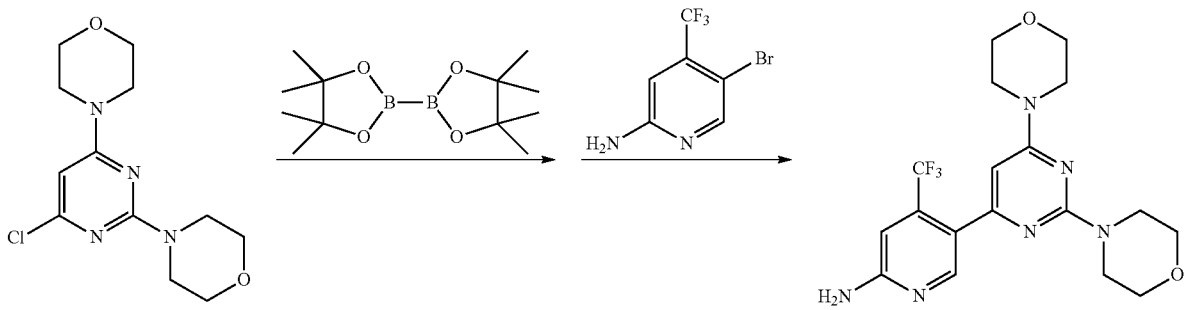

According to some embodiments of the present disclosure, the step (2) comprising: (a') dissolving the compound of formula 6, 14.4 g, 0.06 mol, the compound of formula 5, 18.2 g, 0.072 mol, KOAc 17.64 g, 0.18 mol and $PdCl_2(PPh_3)_2$, 4.2 g, 0.006 mol in DMSO 200 mL; (b') keeping a resulting mixture of step (a') under a temperature of 5° C. for about 7 hours; and (c') adding the compound of formula 4, 17 g, 0.06 mol into a mixture of step (b'), and keeping the resulting mixture under a temperature of 5° C. for about 16 hours.

According to some embodiments of the present disclosure, in the method disclosed herein, the compound 5 in step (2-1) may be used at an amount of 1.0 equivalent to 3 equivalents per 1 equivalent by mole of the compound 6. In other embodiments, the amount is 1.2 equivalents per 1 equivalent by mole of the compound 6.

According to some embodiments of the present disclosure, in the method disclosed herein, the compound 4 in step (2-3) may be used at an amount of 1.0 equivalent to 1.1 equivalents per 1 equivalent by mole of the compound 6. In other embodiments, the amount is 1.05 equivalents per 1 equivalent by mole of the compound 6.

According to some embodiments of the present disclosure, in the method disclosed herein, KOAc in step (2-1) may be used at an amount of 1 equivalent to 4 equivalents per 1 equivalent by mole of the compound 6. In other embodiments, the amount is 3 equivalents per 1 equivalent by mole of the compound 6.

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

In the present invention, the term "comprise" is an open expression, it means comprising the contents disclosed herein, but don't exclude other contents.

Compared with the prior art, the advantages of the present invention is as follows: in step (1) of the present invention, inventors use TEA as a base, which can reduce the amount of morpholine, avoid the production of isomers resulting from excess diisopropylethylamine, and greatly improve the yield of the reaction. In step (B) of the present invention, inventors use one-pot method, which can shorten the synthetic route with respect to WO2007084786, avoid the isolation of the intermediate (boric acid compound), and save the reaction time. In the present invention, inventors simplify the post-processing operation, which can reduce waste, while improve the yield of the buparlisib of formula 1. The whole reaction route of the present invention does not use harsh conditions such as high temperature and high pressure, it is simple and easy to control for the industrial production.

EXAMPLES

The new preparation methods of PI3K inhibitor buparsilib and intermediates thereof are disclosed in the examples of the present disclosure. Those skilled in the art can learn from this article to properly improve the process parameters to implement the preparation method. It's to note that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

Example 1

Preparation of Compound 4

Added compound 2 (18.3 g, 0.10 mol), TEA (200 ml) and $CH_2Cl_2$ (200 ml) into a first reactor, and lowered the temperature to −5° C. Then, dripped the first $CH_2Cl_2$ solution of morpholine (9.57 g, 0.11 mol) slowly (≥30 min) into the first reactor, kept the reaction at room temperature for 2 hours. Then lowered the temperature to −5° C., dripped the second $CH_2Cl_2$ solution of morpholine (8.7 g, 0.10 mol) slowly (≥30 min) into the first reactor, kept the reaction at room temperature for 3 hours. Washed the reaction solution by saturated salt water for 2 times, dried over $Na_2SO_4$, and concentrated to obtain compound 4 (26.2 g, yield 92%). NMR Spectrum: ($DMSOd_6$) 3.58-3.77 (m, 16H), 6.73 (s, 1H); Mass Spectrum: $M+H^+$ 285.

Example 2

Preparation of Compound 4

Added compound 2 (18.3 g, 0.10 mol), TEA (200 ml) and $CH_2Cl_2$ (200 ml) into a first reactor, and lowered the temperature to −2° C. Then, dripped the first $CH_2Cl_2$ solution of morpholine (8.7 g, 0.10 mol) slowly (≥30 min) into the first reactor, kept the reaction at room temperature for 1 hour. Then lowered the temperature to −2° C., dripped the second $CH_2Cl_2$ solution of morpholine (9.14 g, 0.105 mol) slowly (≥30 min) into the first reactor, kept the reaction at room temperature for 2 hours. Washed the reaction solution by saturated salt water for 3 times, dried over $Na_2SO_4$, and concentrated to obtain compound 4 (25.9 g, yield 91%).

Example 3

Preparation of Compound 4

Added compound 2 (18.3 g, 0.10 mol), TEA (200 ml) and $CH_2Cl_2$ (200 ml) into a first reactor, and lowered the temperature to 0° C. Then, dripped the first $CH_2Cl_2$ solution of morpholine (9.14 g, 0.105 mol) slowly (≥30 min) into the first reactor, kept the reaction at room temperature for 0.5 hour. Then lowered the temperature to 0° C., dripped the second $CH_2Cl_2$ solution of morpholine (9.57 g, 0.11 mol) slowly (≥30 min) into the first reactor, kept the reaction at room temperature for 1 hour. Washed the reaction solution by saturated salt water for 2 times, dried over Na$_2$SO$_4$, and concentrated to obtain compound 4 (25.6 g, yield 90%).

Example 4

Preparation of Buparlisib

Added compound 6 (14.4 g, 0.06 mol), bis(pinacolato) diboron (compound 5) (18.2 g, 0.072 mol), DMSO (200 mL), KOAc (17.64 g, 0.18 mol) and PdCl$_2$(PPh$_3$)$_2$ (4.2 g, 0.006 mol) into a second reactor, then heated the resulting mixture to 5° C. and kept the reaction for 7 hours, and then added compound 4 (17 g, 0.06 mol) into the second reactor, kept the reaction for 16 hours. Put the reaction solution into water after the reaction was finished, and large amount of solid were separated. The resulting mixture was filtered, stirred with methanol/acetone (V:V=1:1) and crystallized for 3 hours. The filter cake was dried in vacuo at 60° C. for 8 hours to obtain the buparlisib product (compound 1) as a white solid (23.15 g, yield 94%), HPLC purity: 99.2%. Mass Spectrum: M+H⁻ 411.

Example 5

Preparation of Buparlisib

Added compound 6 (14.4 g, 0.06 mol), bis(pinacolato) diboron (compound 5) (15.2 g, 0.06 mol), DMSO (220 mL), KOAc (5.88 g, 0.06 mol) and PdCl$_2$(PPh$_3$)$_2$ (4.2 g, 0.006 mol) into a second reactor, then heated the resulting mixture to 15° C. and kept the reaction for 3 hours, and then added compound 4 (18.7 g, 0.066 mol) into the second reactor, kept the reaction for 12 hours. Put the reaction solution into water after the reaction was finished, and large amount of solid were separated. The resulting mixture was filtered, stirred with methanol/acetone (V:V=1:1) and crystallized for 3 hours. The filter cake was dried in vacuo at 60° C. for 8 hours to obtain the buparlisib product (compound 1) as a white solid (22.90 g, yield 93%), HPLC purity: 99.5%.

Example 6

Preparation of Buparlisib

Added compound 6 (14.4 g, 0.06 mol), bis(pinacolato) diboron (compound 5) (45.6 g, 0.18 mol), DMSO (250 mL), KOAc (23.52 g, 0.24 mol) and PdCl$_2$(PPh$_3$)$_2$ (4.2 g, 0.006 mol) into a second reactor, then heated the resulting mixture to 10° C. and kept the reaction for 5 hours, and then added compound 4 (17.85 g, 0.063 mol) into the second reactor, kept the reaction for 18 hours. Put the reaction solution into water after the reaction was finished, and large amount of solid were separated. The resulting mixture was filtered, stirred with methanol/acetone (V:V=1:1) and crystallized for 3 hours. The filter cake was dried in vacuo at 60° C. for 8 hours to obtain the buparlisib product (compound 1) as a white solid (22.65 g, yield 92%), HPLC purity: 99.3%.

In the specification, Unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing buparlisib of formula 1, comprising:
   (1) contacting a compound of formula 2 with a compound of formula 3 to obtain a compound of formula 4; and
   (2) contacting a compound of formula 6 with a compound of formula 5 and the compound of formula 4 to obtain the buparlisib of formula 1,

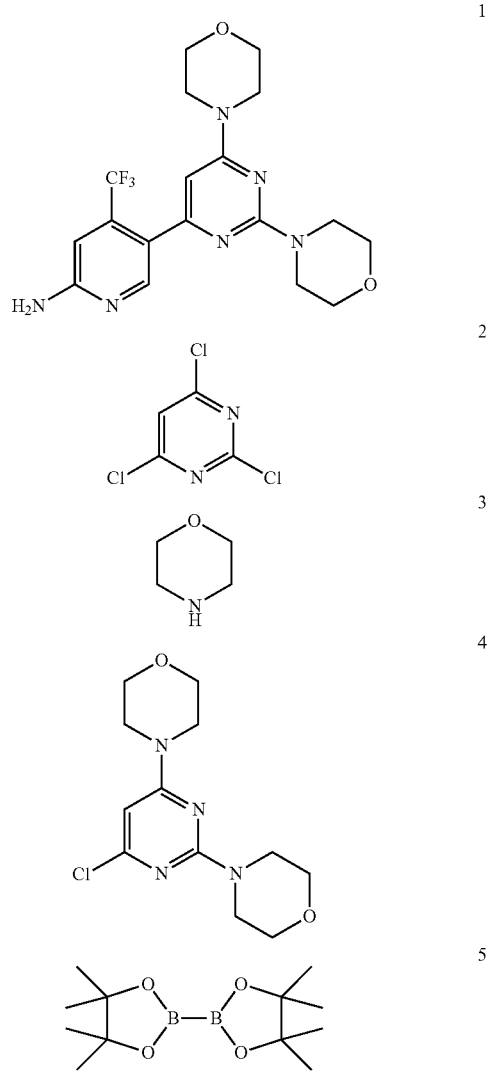

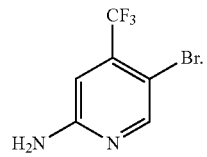

wherein the step (2) comprising:
(2-1) dissolving the compound of formula 6, the compound of formula 5, KOAc and PdCl2(PPh3)2 in DMSO;
(2-2) keeping a resulting mixture of step (2-1) under a temperature ranging from about 5° C. to about 15° C. for about 3 hours to about 7 hours; and
(2-3) adding the compound of formula 4 into a mixture of step (2-2), and keeping the resulting mixture under a temperature ranging from about 5° C. to about 15° C. for about 12 hours to about 18 hours.

2. The method of claim 1, wherein the compound of formula 2 is contacted with the compound of formula 3 in a first organic solvent and in presence of a base.

3. The method of claim 2, wherein the first organic solvent is dichloromethane, and the base is triethanolamine.

4. The method of claim 2, wherein the step (1) comprising:
(1-1) dissolving the compound of formula 2 and the base in the first organic solvent;
(1-2) adding a first dichloromethane solution of the compound of formula 3 into a resulting mixture of step (1-1) under a temperature ranging about −5° C. to about 0° C.;
(1-3) keeping a resulting mixture of step (1-2) at room temperature for about 0.5 hour to about 2 hours;
(1-4) adding a second dichloromethane solution of the compound of formula 3 into a resulting mixture of step (1-3) under a temperature ranging about −5° C. to about 0° C.; and
(1-5) keeping a resulting mixture of step (1-4) at room temperature for about 1 hour to about 3 hours.

5. The method of claim 4, wherein in the first dichloromethane solution of the compound of formula 3, the compound of formula 3 is used at an amount of 1.0 equivalent to 1.1 equivalents per 1 equivalent by mole of the compound of formula 2.

6. The method of claim 5, wherein in the first dichloromethane solution of the compound of formula 3, the compound of formula 3 is used at an amount of 1.05 equivalents per 1 equivalent by mole of the compound of formula 2.

7. The method of claim 4, wherein in the second dichloromethane solution of the compound of formula 3, the compound of formula 3 is used at an amount of 1.0 equivalent to 1.1 equivalents per 1 equivalent by mole of the compound of formula 2.

8. The method of claim 7, wherein in the second dichloromethane solution of the compound of formula 3, the compound of formula 3 is used at an amount of 1.05 equivalents per 1 equivalent by mole of the compound of formula 2.

9. The method of claim 1, wherein the compound of formula 5 in step (2-1) is used at an amount of 1.0 equivalent to 3 equivalents per 1 equivalent by mole of the compound of formula 6.

10. The method of claim 9, wherein the compound of formula 5 in step (2-1) is used at an amount of 1.2 equivalents per 1 equivalent by mole of the compound of formula 6.

11. The method of claim 1, wherein KOAc in step (2-1) is used at an amount of 1.0 equivalent to 4.0 equivalents per 1 equivalent by mole of the compound of formula 6.

12. The method of claim 11, wherein KOAc in step (2-1) is used at an amount of 3.0 equivalents per 1 equivalent by mole of the compound of formula 6.

13. The method of claim 1, wherein the compound of formula 4 in step (2-3) is used at an amount of 1.0 equivalent to 1.1 equivalents per 1 equivalent by mole of the compound of formula 6.

14. The method of claim 13, wherein the compound of formula 4 in step (2-3) is used at an amount of 1.05 equivalents per 1 equivalent by mole of the compound of formula 6.

15. The method of claim 1, wherein the step (1) comprising:
(a) dissolving the compound of formula 2, 18.3 g, 0.10 mol and triethanolamine 200 ml in dichloromethane 200 ml;
(b) adding a first dichloromethane solution of the compound of formula 3, 9.57 g, 0.11 mol into a resulting mixture of step (a) under a temperature of −5° C.;
(c) keeping a resulting mixture of step (b) at room temperature for about 2 hours;
(d) adding a second dichloromethane solution of the compound of formula 3, 8.7 g, 0.10 mol into a resulting mixture of step (c) under a temperature of −5° C.; and
(e) keeping a resulting mixture of step (d) at room temperature for about 3 hours.

16. The method of claim 1, wherein the step (2) comprising:
(a') dissolving the compound of formula 6, 14.4 g, 0.06 mol, the compound of formula 5, 18.2 g, 0.072 mol, KOAc 17.64 g, 0.18 mol and PdCl2(PPh3)2, 4.2 g, 0.006 mol in DMSO 200 mL;
(b') keeping a resulting mixture of step (a') under a temperature of 5° C. for about 7 hours; and
(c') adding the compound of formula 4, 17 g, 0.06 mol into a mixture of step (b'), and keeping the resulting mixture under a temperature of 5° C. for about 16 hours.

* * * * *